(12) United States Patent
Piers et al.

(10) Patent No.: US 9,122,074 B2
(45) Date of Patent: Sep. 1, 2015

(54) DIFFRACTIVE BINOCULAR LENS SYSTEMS AND METHODS

(71) Applicant: AMO Groningen B.V., Groningen (NL)

(72) Inventors: Patricia A Piers, Groningen (NL); Hendrik A Weeber, Groningen (NL); Marrie H Van Der Mooren, Engelbert (NL)

(73) Assignee: AMO GRONINGEN B.V., Groningen (NL)

( * ) Notice: Subject to any disclaimer, the term of this patent is extended or adjusted under 35 U.S.C. 154(b) by 0 days.

(21) Appl. No.: 14/148,408

(22) Filed: Jan. 6, 2014

(65) Prior Publication Data

US 2014/0118684 A1 May 1, 2014

Related U.S. Application Data

(62) Division of application No. 12/613,805, filed on Nov. 6, 2009, now Pat. No. 8,623,083.

(51) Int. Cl.
*A61F 2/16* (2006.01)
*G02C 7/02* (2006.01)
(Continued)

(52) U.S. Cl.
CPC .............. *G02C 7/022* (2013.01); *A61F 2/1621* (2013.01); *G02C 7/027* (2013.01); *G02C 7/041* (2013.01);
(Continued)

(58) Field of Classification Search
USPC ................................................. 623/6.31–6.33
See application file for complete search history.

(56) References Cited

U.S. PATENT DOCUMENTS

| | | |
|---|---|---|
| 4,641,934 A | 2/1987 | Freeman |
| 4,655,565 A | 4/1987 | Freeman |

(Continued)

FOREIGN PATENT DOCUMENTS

| | | | |
|---|---|---|---|
| EP | 0453136 A2 | 10/1991 | |
| EP | 1449498 A2 | 8/2004 | |

(Continued)

OTHER PUBLICATIONS

International Preliminary Report on Patentability and Written Opinion for Application No. PCT/IB2010/002995, mailed in May 8, 2012, 9 pages.

(Continued)

*Primary Examiner* — David H Willse
*Assistant Examiner* — Tiffany Shipmon

(57) ABSTRACT

A system of ophthalmic lenses contains a first lens for a first eye of a subject and a second lens for a second eye of a subject. The first lens includes a first lens shape having a first base refractive power and a first diffractive pattern imposed on the first lens shape, the diffractive pattern having a first lower diffraction order with a first lower diffractive power and a first higher diffraction order with a first higher diffractive power. The first lens includes lower and higher optical powers equal to the first base refractive power plus the first lower and higher diffractive powers, respectively. The second lens includes a second lens shape having a second base refractive power and a second diffractive pattern imposed on the second lens shape, the second diffractive pattern having a second lower diffraction order with a second lower diffractive power and a second higher diffraction order with a second higher diffractive power. The second lens includes lower and higher optical powers equal to the second base refractive power plus the second lower and higher diffractive powers, respectively. The first higher optical power has a negative LCA and the second lower optical power has a negative LCA. The second base refractive power does not equal either the second lower optical power or the higher optical power.

5 Claims, 4 Drawing Sheets

(51) Int. Cl.
G02C 7/04 (2006.01)
G02C 7/06 (2006.01)

(52) U.S. Cl.
CPC ................. *G02C 7/06* (2013.01); *A61F 2/1618* (2013.01); *A61F 2/1654* (2013.01); *G02C 2202/20* (2013.01)

(56) References Cited

U.S. PATENT DOCUMENTS

| | | |
|---|---|---|
| 4,881,804 A | 11/1989 | Cohen |
| 4,995,715 A | 2/1991 | Cohen |
| 5,144,483 A | 9/1992 | Cohen |
| 5,229,797 A | 7/1993 | Futhey et al. |
| 5,296,881 A | 3/1994 | Freeman |
| 5,443,507 A | 8/1995 | Jacobi |
| 6,537,317 B1 | 3/2003 | Steinert et al. |
| 6,609,793 B2 | 8/2003 | Norrby et al. |
| 7,377,640 B2 | 5/2008 | Piers et al. |
| 7,455,404 B2 | 11/2008 | Bandhauer et al. |
| 2006/0098162 A1 | 5/2006 | Bandhauer et al. |

FOREIGN PATENT DOCUMENTS

| | | | | |
|---|---|---|---|---|
| RU | 2186417 | * | 7/2002 | ............... G02C 7/04 |
| RU | 2186417 C2 | | 7/2002 | |
| WO | WO-2006047698 A1 | | 5/2006 | |

OTHER PUBLICATIONS

International Search Report and Written Opinion for Application No. PCT/IB2010/002995, mailed on Aug. 19, 2011, 16 pages.

Jacobi F.K., et al., "Bilateral Implantation of Assymmetrical Diffractive Multifocal Intraocular Lenses," Archives of Ophthalmology. 1999, vol. 117 (1), pp. 17-23.

Navarro R., et al., "Accommodation-Dependent Model of the Human Eye with Aspherics," Journal of the Optical Society of America, 1985, vol. 2 (8). pp. 1273-1281.

Whitefoot H.D., et al., "Hyperchromatic Lenses as Potential Aids for the Presbyope." Ophthalmic and Physiological Optics, 1995, vol. 15 (1), pp. 13-22.

* cited by examiner

DIFFRACTIVE BINOCULAR LENS SYSTEMS AND METHODS

This application claims priority to and is a divisional application of U.S. application Ser. No. 12/613,805, filed on Nov. 6, 2009, the entirety of which is hereby incorporated by reference.

BACKGROUND OF THE INVENTION

1. Field of the Invention

The present invention relates generally to ophthalmic lens systems and associated methods, and more specifically to binocular ophthalmic lens systems and methods in which the aberrations or other optical properties of the two lenses of a lens system are different in at least one respect.

2. Description of the Related Art

Accommodation of the eye is a process in which the axial location and/or optical power of the natural lens changes in response to ciliary muscle action, thereby allowing the eye to focus on objects over a range of distances. The ability for the eye to provide accommodation generally diminishes with age, becoming particularly apparent between the ages of 40 and 50. In addition, accommodative ability may be lost altogether when the natural lens is removed an replace by an intraocular lens, for example, due to the presence of cataracts. In this case, the loss of accommodation is because the vast majority of intraocular lenses that replace the natural lens have a fixed optical power and are unable to move in response to ciliary muscle action.

Multifocal contact lenses and intraocular lenses have been used to at least partially restore a subject's ability to focus on objects at more than one distance. Typically, such lenses provide two optical powers or foci simultaneously—the lower optical power providing the ability to focus on object at distances greater than a few meters, while the higher optical power provides the ability to focus on objects that are within a meter of the subject.

One way of providing a multifocal lens is to add a multifocal diffractive pattern to a refractive lens. The diffractive pattern may be configured so that approximately half the light from an object is focused by the refractive power of the lens (e.g., for providing distant vision), while the other half is focused by the combination of the refractive power of the lens and a +1 diffraction order of the diffractive pattern (e.g., for providing near or intermediate vision). An added benefit to this approach is that the +1 diffraction order has a chromatic aberration that is opposite in sign to that produced by the refractive power of the ophthalmic lens and the cornea of the eye. By proper selection of the diffractive power, the total chromatic aberration of the ophthalmic lens/eye system can be significantly reduced, resulting in improved visual acuity for near or intermediate vision. However, one drawback to traditional multifocal diffractive lenses is that the chromatic aberration for the distance power of the lens is not affected, since there is no diffractive power in this focus.

Accordingly, there is a need to provide multifocal ophthalmic lens systems that provide chromatic aberration reduction for both distant vision and near or intermediate vision.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

Figure 1:
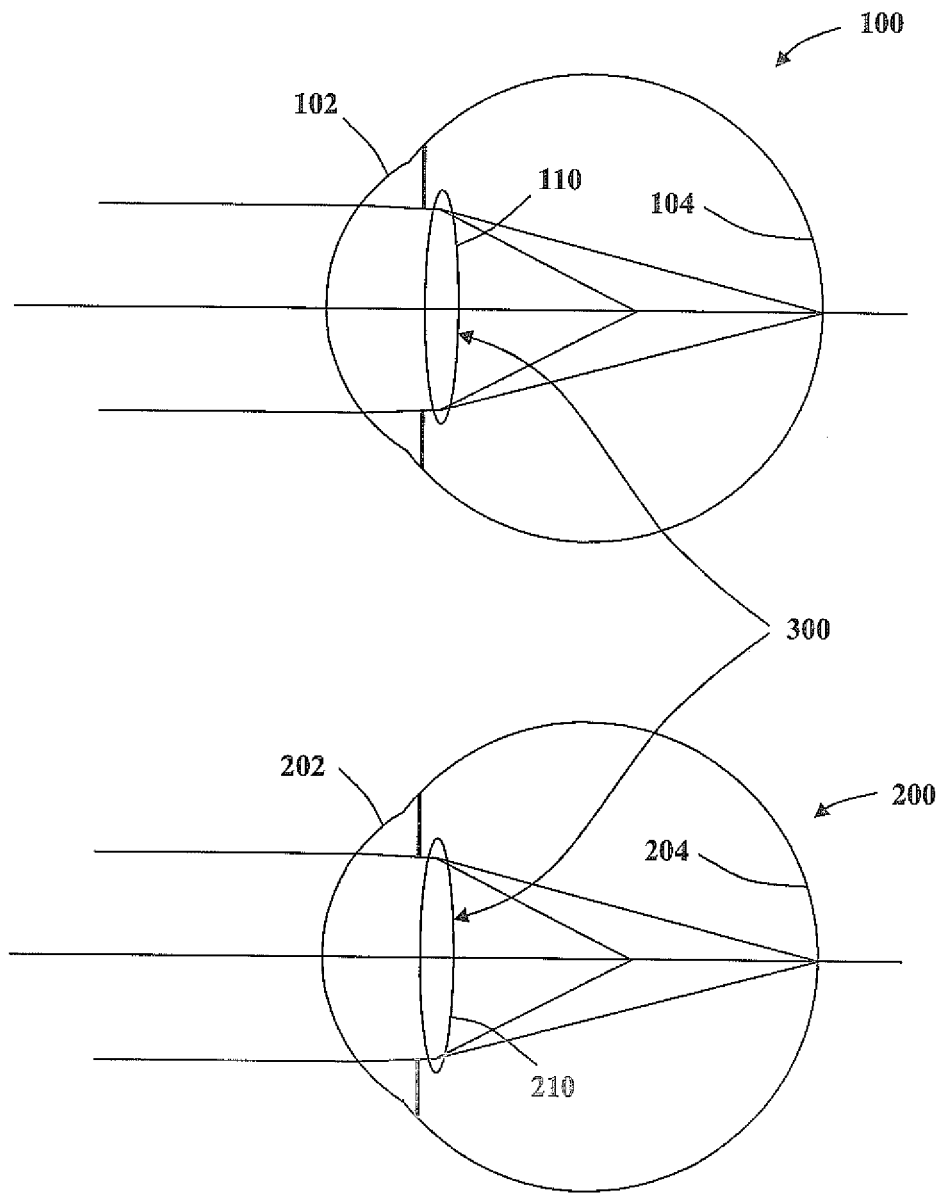
FIG. 1 is a side view of a pair of lenses for different eyes of a subject.

Embodiments of the present invention are directed to ophthalmic lens systems and related methods comprising lenses for providing binocular vision, wherein a pair of lenses for a left and right eye of a human or animal subject have aberrations that are different from one another in at least one respect. For example, the pair of the ophthalmic lenses may each be a multifocal or bifocal lens, wherein each has a lower optical power (longer focal length) and a higher optical power (shorter focal length). For the first lens, an aberration of the cornea of the first eye is reduced or modified to provide improved vision for the lower optical power of the lens (e.g., for providing enhanced distant vision). For the second lens, the same or similar aberration of the cornea of the second eye is reduced or modified to provide improved visual quality for the higher optical power of the lens (e.g., for providing enhanced intermediate or near vision). More specifically, a pair or set of diffractive multifocal ophthalmic lenses may be selected or configured such that the first lens reduces or otherwise favorably changes chromatic aberrations associated with the lower optical power of the lens and/or one eye (distant vision), while the second lens reduces or otherwise favorably changes chromatic aberrations associated with the higher optical power of the lens (near or intermediate vision). Thus, the combination of lenses provides binocular vision in which chromatic aberrations are corrected or reduced both for distant vision and for near and/or intermediate vision.

Embodiments of the present invention discussed below are generally directed to intraocular lenses; however, embodiments of the present invention extend to other types of lenses or lens systems, for example, contact lenses, corneal implants, corneal refractive procedures such as LASIK or PRK, and the like. In some embodiments, two or more different types of ophthalmic lenses may be included in a lens system for improving or enhance vision at different distances for different eyes. For example, one eye of a subject may contain an intraocular lens that reduces an aberration for distant vision, while the other eye contains a contact lens or receives a corneal procedure that reduces an aberration for intermediate or near vision.

As used herein, the term "near vision" means vision provided by an ophthalmic lens when placed within an eye of a subject, wherein a best optical performance or visual acuity occurs for objects located within a range of 25 cm to 40 cm from the subject, or at a distance at which the subject would generally place printed material for the purpose of reading. The distance range of 25 cm to 40 cm corresponds to a spectacle add power of 4 Diopters to 2.5 Diopters, respectively. As used herein, the term "intermediate vision" means vision provided by an ophthalmic lens when placed within the eye, wherein a best optical performance or visual acuity occurs for objects located within a range of 40 cm (a spectacle add power of 2.5 Diopters) to 2 meters (a spectacle add power of 0.5 Diopters) from the subject. As used herein, the term "distant vision" means vision provided by an ophthalmic lens when placed within the eye, wherein a best optical performance or visual acuity occurs for objects located at a distance of 6 meters or greater from the subject. As used herein, an intraocular lens add power is equal to a corresponding spectacle add power multiplied by 0.8.

As used herein, the phrase "positive diffraction order" means a diffraction order of a diffractive pattern, diffractive grating, or phase plate that is higher than a zeroth diffraction order of the diffractive pattern and has a positive optical power. As used herein, the phrase "zeroth diffraction order" refers to light that is not diffracted by a diffractive pattern and thus has zero or substantially zero diffractive optical power. As used herein, the phrase "+1 diffraction order" means the lowest positive diffraction order above the zeroth diffraction order that has a positive diffractive power. As used herein, other higher positive diffraction orders (e.g., "+2 diffraction order", "+3 diffraction order", etc.) have progressively higher positive diffractive power of the diffractive grating compared to the +1 diffraction order. As used herein, negative diffraction orders (e.g., "−1 diffraction order", "−2 diffraction order", etc.) are diffraction orders having progressively more negative diffractive power. As used herein, the phrases "primary diffraction order", "first diffraction order", "secondary diffraction order", "second diffraction order", and the like, refer to diffraction orders of a subject diffractive grating irrespective of which particular diffraction order they may correspond to. For example, a primary diffraction order or first diffraction order may correspond to a zeroth diffraction order, while a secondary diffraction order or second diffraction order may correspond to a +1 diffraction order. Alternatively, a primary or first diffraction order may correspond to a +1 diffraction order and a secondary or second diffraction order may correspond to a +2 diffraction order.

As used herein, the phrase "lens shape" means the overall figure of an optic, optical element, or lens that provides a base refractive power, and which is typically suitable for providing distant vision when used on or in an eye. The lens shape comprises an anterior surface shape or curvature of an anterior surface of the optic and a posterior surface shape or curvature of a posterior surface of the optic. The surface shape or curvature may be spherical or have an aspheric shape, for example to reduce or modify an aberration of the lens itself or of a typical or particular cornea or eye. One or more refractive or diffractive patterns or profiles may be imposed on, or added to, the lens shape to provide more complex optical characteristics, such as to provide multifocal or bifocal performance.

As used herein, the phrase "optical power" means the ability of an optic, optical element, or lens to cause light to converge or diverge from a focus (either real or virtual). The optical power may be a refractive power, a diffractive power, or some combination or addition of refractive and diffractive power. As used herein, the phrase "diffractive power" means optical power of an optic, optical element, or lens attributable to a diffractive pattern or profile, for example, attributable to a diffractive pattern or profile that is imposed on or added to a base shape of an optic. As used herein, the phrase "refractive power" means optical power of an optic, optical element, or lens attributable to a profile or shape of one of the surfaces of the optic. As used herein, the terms "about" and "approximately" means plus or minus 0.25 Diopters when used in reference to an optical power (e.g., a refractive power, diffractive power, or combination thereof) or a difference in optical powers (e.g., an add power). As used herein, the phrase "about equal" or "approximately equal" means within plus or minus 0.25 Diopters when used in reference to a comparison between two optical powers of differences in optical powers.

As used herein, the term "light" means electromagnetic radiation within the visible band of the electromagnetic spectrum. As used herein, the phrase "optical element" includes any element that may be used to form an image from an object or to direct collimated light or light from a point source to a focal point, either real or virtual. The optical element may function based on refraction, reflection, and/or diffraction of light incident on the optical element.

As used herein, the phrase "longitudinal chromatic aberration" (LCA) means the range of distances along the optical axis of a diffractive and/or refractive lens, optic, or optical element over which collimated light from a broadband light source focuses for a given wavelength range. The LCA may be an absolute LCA expressed as an absolute range of distances (e.g., in millimeters, microns, or Diopters) or may be a ratio or percent of the range of distances compared to a nominal, average, or other representative focal length or power of the optical element. Unless otherwise indicated, the LCA is based on a wavelength range from 450 nanometers to 650 nanometers and, when expressed as a ratio or percentage, the representative focal length or power is that of the optical element at a wavelength of 550 nm. As used herein, a LCA is positive when the focal length (1/power) of the optical element increases with increasing wavelength over at least a portion of visible waveband of electromagnetic radiation. As used herein, a LCA is zero when the focal length or power of the optical element is the same at two or more distinct wavelengths of light that are separated by at least 50 nanometers. As used herein, an optical element is "achromatic" or is an "achromat" if it has a LCA that is zero. As used herein, "approximately" or "about" means within ±0.05 when used in reference to an amount of a relative longitudinal aberration (e.g., an amount of relative LCA or relative longitudinal spherical aberration).

Referring to FIG. 1, a first eye 100 (e.g., a left eye) and a second eye 200 (e.g., a right eye) of a human or animal subject are shown. Eyes 100, 200 each include a cornea 102, 202 for focusing light toward a corresponding retina 104, 204. Eyes 100, 200 further include an iris 106, 206 for controlling the amount of light entering eyes 100, 200. Eyes 100, 200 may also each include a capsular bag connected to a ciliary muscle by a plurality of zonules (not shown for clarity).

The eyes 100, 200 also include a lens pair, set, or system 300 of intraocular lenses (IOLs) comprising first and second multifocal or bifocal IOLs 110, 210. In the illustrated embodiment, IOLs 110, 210 replace the natural lenses of each eye and generally are disposed within the capsular of each eye 100, 200 using means well known within the art. Alternatively, one or both of IOLs 110, 210 may be disposed in front of the capsular bag or in front of iris 106, 206, for example, when one or both IOLs 110, 210 are used in combination with the natural lenses of one or both eyes 100, 200. The elements shown in FIG. 1, such as eyes 100, 200 and IOLs 110, 210, may be physical elements, or may be mathematical representations of these elements, for example, they may be part of a model represented used in a ray tracing or physical optics program.

Figure 2:
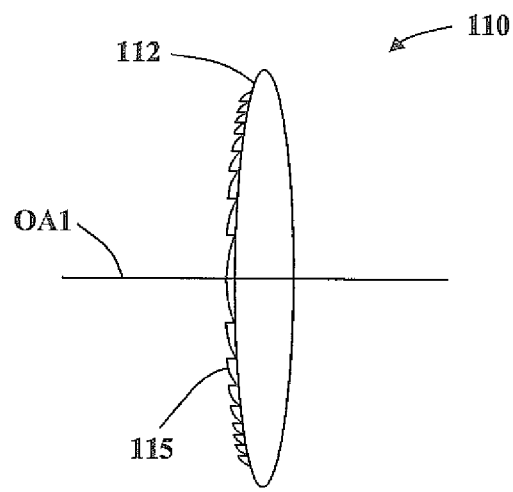
FIG. 2 is a more detailed view of lens in the left eye of a subject, the lens including a diffractive pattern in accordance to an embodiment of the present invention.
Figure 3:
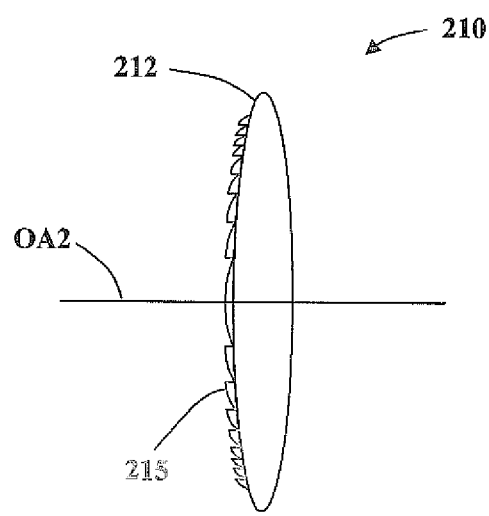
FIG. 3 is a more detailed view of lens in the right eye of a subject, the lens including a diffractive pattern in accordance to an embodiment of the present invention.

With further reference to FIGS. 2 and 3, first IOL 110 is disposed about an optical axis OA1 and comprises a first lens shape 112 having a first base refractive power P1.r. The first IOL 110 also comprises a first multifocal diffractive pattern or grating 115 that is imposed on or added to a first lens shape 112. First IOL 110 includes a first lower optical power P1.low and a first higher optical power P1.high that is greater than first lower optical power P1.low. First lower optical power P1.low is equal to a sum of first base refractive power P1.r and a first lower diffractive power P1.d.low of a first lower diffraction order of first diffractive pattern 115. First higher optical power P1.high is equal to a sum of first base refractive power P1.r and a first higher diffractive power P1.d.high of a first higher diffraction order of first diffractive pattern 115.

Second IOL 210 is disposed about an optical axis OA2 and comprises a second lens shape 212 having a second base refractive power P2.r. The second IOL 210 also comprises a second multifocal diffractive pattern or grating 215 imposed on or added to a second lens shape 212. Second IOL 210 includes a second lower optical power P2.low and a second higher optical power P2.high that is greater than second lower optical power P2.low. Second lower optical power P2.low is equal to a sum of second base refractive power P2.r and a second lower diffractive power P2.d.low of a second lower diffraction order of second diffractive pattern 215. Second higher optical power P2.high is equal to a sum of second base refractive power P2.r and a second higher diffractive power P2.d.high of a second higher diffraction order of second diffractive pattern 215.

IOLs 110, 210 may comprise one or more haptics or suitable structure for positioning or centering the optic portion of the IOL and/or for moving or changing the shape of the optic portion, for example, in an accommodating IOL. IOLs 110, 210 may be made of silicone, acrylic, and/or some other polymer material suitable for insertion into a human or animal eye. While illustrated as biconvex, IOLs 110, 210 may also be plano-convex, concave, plano-concave, or the like. The base refractive powers P1.r, P2.r of IOLs 110, 210 are generally from −20 Diopters to +40 Diopter, usually from −10 Diopters to +30 Diopters, with about +20 Diopters being typical. At least one of IOLs 110, 210 may have a refractive power or total power that is zero or about zero Diopters.

At least one surface of either or both IOLs 110, 210 may be characterized by an equation defining a conoid of rotation, wherein a surface sag profile varies according to the relation:

$$\frac{cr^2}{1+\sqrt{1-(1+k)c^2r^2}} \quad (1)$$

where c is a base curvature of the surface portion (which is equal to 1/R, where R is the radius of curvature, k is a conic constant, and r is the radial distance from the optical axis OA. Alternatively, at least one of the surfaces within the first zone of the intraocular lens may be characterized by an equation defining a modified conoid of rotation, wherein a surface sag profile varies according to the relation:

$$\frac{cr^2}{1+\sqrt{1-(1+k)c^2r^2}} + a_4 r^4 + a_6 r^6 + \ldots \quad (2)$$

where $a_2, a_4, \ldots$ are constants, c is a base curvature of the surface portion (which is equal to 1/R, where R is the radius of curvature, k is a conic constant, and r is the radial distance from the optical axis OA.

Figure 4:
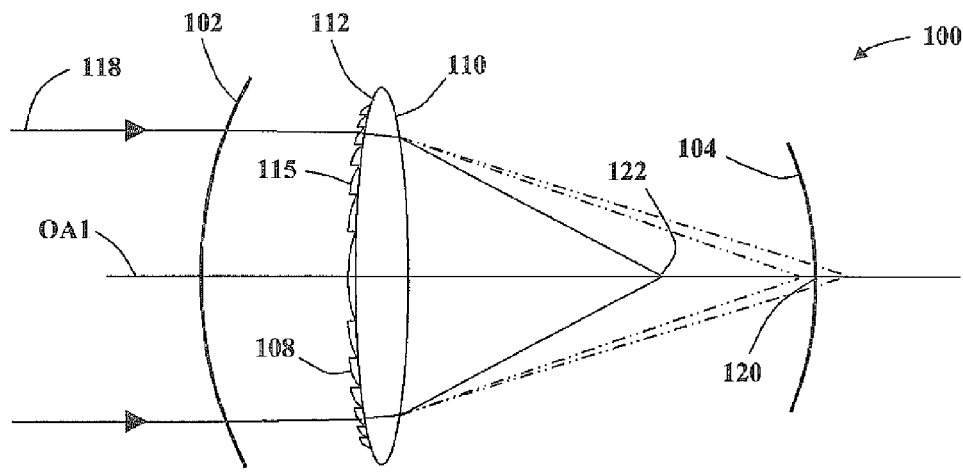
FIG. 4 is a side view of the eyes shown in FIG. 1 illustrating a functioning of two lenses when viewing a distant light source or object.
Figure 4:
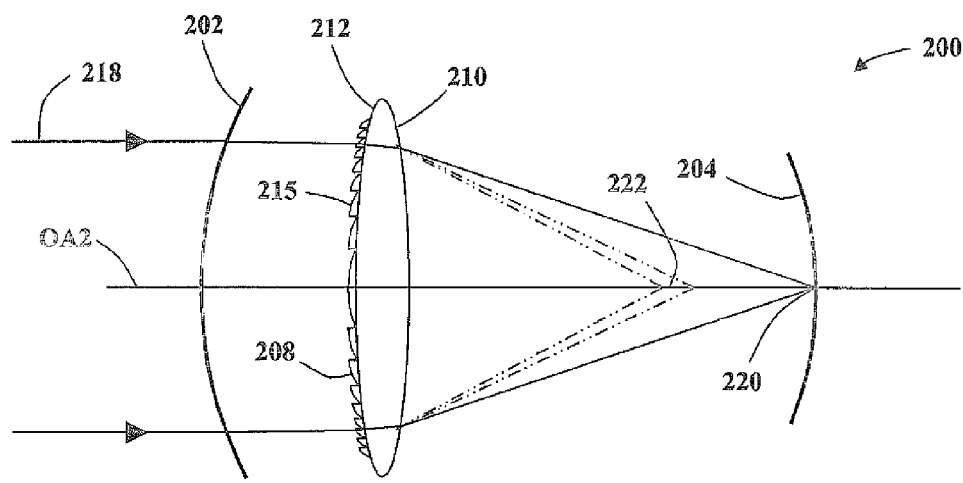

Referring to FIG. 4, advantages and operation of lens system 300 will be discussed. In the illustrated embodiment, first IOL 110 is disposed in the left eye of a subject, while second IOL 210 is disposed in the right eye of the same subject. It will be appreciated that IOLs 110, 210 could alternatively be configured so that first IOL 110 is disposed in the right eye of the subject, while second IOL 210 is disposed in the left eye of the same subject. The IOLs 110, 210 may be disposed within the capsular bag of a pseudophakic eye, or at a location outside the capsular, for example, between the capsular bag and the iris. Alternatively, one or both IOLs 110, 210 may be phakic IOL and used in combination with the natural lens of the eye(s) to provide vision.

A collimated or nearly collimated wavefront from a distant object illuminates first and second eyes 100, 200. For example, a collimated or nearly collimated source may be provided by a point source at a distance 6 meters or more from the eye, or an automobile headlight at a distance of greater than 100 meters from the eye. Rays 118 from the collimated wavefront enter eye 100 and are split by first diffractive pattern 115 between first lower diffractive power P1.d.low and first higher diffractive power P1.d.high to form a first focus 120 and second focus 122, respectively. IOL 110 is configured to provide distant vision by forming first focus 120 at or near retina 104 along optical axis OA1 when collimated rays 118 enter eye 100. By contrast, second focus 122 is located along OA1 anterior to retina 104, IOL 110 generally being configured so that second focus 122 provides near vision and/or intermediate vision (e.g., by configuring first higher optical power P1.high to be greater than first lower diffractive power P1.d.low by at least 1 Diopter or 2 Diopters, generally by at least 3 Diopters or 4 Diopters).

Rays 118, from which first focus 120 is formed, are spread along optical axis OA1, the extent being shown by the dashed lines at the top of the figure. This spread of light may result in a reduction of visual acuity or the modulation transfer function (MTF) of eye 100 for objects and light sources located at relatively distant locations from eyes 100, 200. In the current embodiment, this spread along optical axis OA1 is due to dispersion of light in a broadband or white light source by a longitudinal chromatic aberration (LCA) of the refractive portion of lens 110 and cornea 102, whereby light at different wavelengths is focused to different locations along optical axis OA1. In general, the spread of light along optical axis OA1 may also be caused by other optical effects such as spherical aberrations, astigmatism, or coma.

In contrast to first focus 120, second focus 122 is shown in FIG. 4 to converge or focus to a single point or substantially a single point. In the current embodiment, the relatively sharp focus of second focus 122 is provided by configuring first diffractive pattern 115 to have a negative LCA that reduces, compensates, or eliminates a positive LCA of the refractive power of lens 110 and/or a positive LCA of cornea 110 or eye 100. It will be understood that illustration of second focus 122 as a point is an idealization, and that in a real eye diffraction effects and some residual LCA or other longitudinal aberrations would typically still exist. However, the point representation of second focus 122 serves to illustrate that LCA for second focus 122 is much less that LCA for first focus 120 in this case. In the illustrated embodiment, lens 110 has a LCA for the second diffraction order that is negative and a LCA for the first diffraction order that is positive. Alternatively, lens 110 may have a LCA that is negative for both the first and second diffraction orders.

Figure 5:
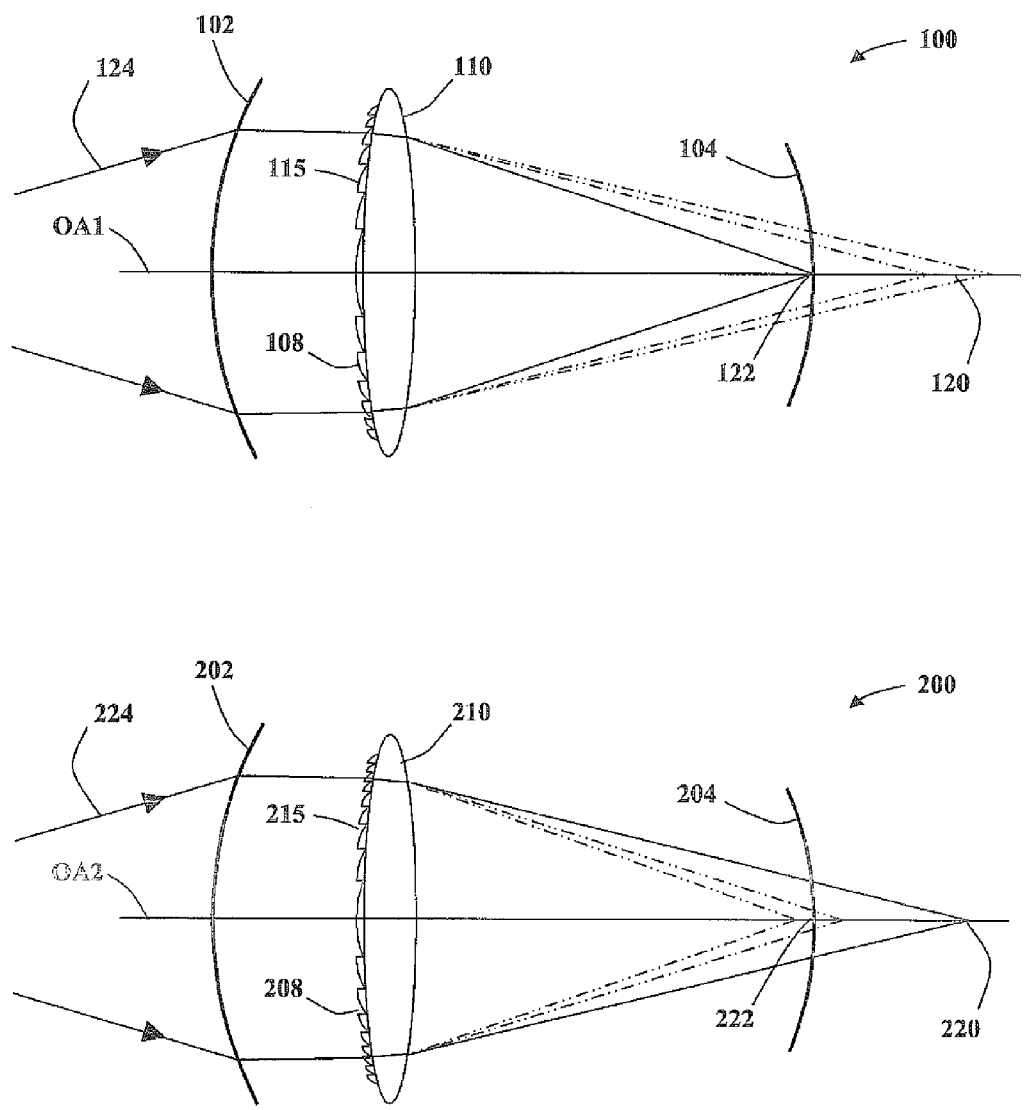
FIG. 5 is a side view of the eyes shown in FIG. 1 illustrating a functioning of two lenses when viewing a light source or object that is relatively close to a subject.

With further reference to FIG. 5, the collimated wavefront shown in FIG. 4 is replaced by a diverging wavefront that directs diverging rays 124 toward eye 100. The diverging wavefront may be produced by a point source or a spatially extended source that is located relatively close to eyes 100, 200, for example, at a distance of 250 millimeters away from eyes 100, 200 a distance of 1 or 2 meters away from eyes 100, 200. In this case, second focus 122 is located at or near retina 104 along optical axis OA1, while first focus 120 is located posteriorly of retina 104.

By way of summary, for distant objects or light sources (FIG. 4; distant vision), IOL 110 produces a first focus 120 that is located on or near retina 104 and an image that is at least somewhat blurred due to relatively large LCA. By contrast, for relatively close objects or light sources (FIG. 5; near or intermediate vision), IOL 110 moves second focus 122 on or near retina 104, which provides a relatively sharp image that has a relatively small amount or no LCA. In this manner, first lens 110 provides distant vision that has chromatic aberrations that are the same or similar to those of a typical IOL without a diffractive pattern, while providing near and/or intermediate vision that has little or no LCA, resulting in improved or relatively high visual acuity and/or MTF performance (e.g., compared to a conventional refractive lens configured to provide the near and/or intermediate vision).

Still referring to FIGS. 4 and 5, the functioning of IOL 210 in eye 200 will now be discussed. Rays 218, which are from the same source as the collimated wavefront entering eye 100, enter eye 200 and are split by second diffractive pattern 215 between first lower diffractive power P2.d.low and first higher diffractive power P2.d.high to form a first focus 220 and second focus 222, respectively. IOL 210 is configured to provide distant vision by forming first focus 220 on or near retina 204 along optical axis OA2 when collimated rays 218 enter eye 200. By contrast, second focus 222 is located along OA2 anterior to retina 104, whereby IOL 210 is configured so that second focus 222 provides near vision and/or intermediate vision, as discussed above in regard to second focus 122.

In contrast to IOL 110, both diffraction orders in the illustrated embodiment of second diffractive pattern 215 are advantageously positive, so that both the second lower diffractive power P2.d.low and the second higher diffractive power P2.d.high have non-zero values that are both positive. One benefit of both the second lower diffractive power P2.d.low and the second higher diffractive power P2.d.high being positive is that each of the two diffraction orders of second diffractive pattern 215 produces a negative LCA that reduces or compensate for a positive LCA of IOL 210 and/or cornea 202.

It will be appreciated that the second base refractive power P2.r is less than either first lower optical power P1.low or first higher optical power P1.high, since the first lower optical power P2.low is equal to the second base refractive power P2.r plus the positive diffractive power of the second lower diffractive power P2.d.low, while the first higher optical power P2.high is equal to the second base refractive power P2.r plus the positive diffractive power of second higher diffractive power P2.d.high. Thus, the second base refractive power P2.r does not produce either near vision optical power, intermediate vision optical power, or distant vision optical power. Rather, distant vision optical power is produced by the addition of the second lower diffractive power P2.d.low to the second base refractive power P2.r to provide distant vision, while near or intermediate vision optical power is produced by the addition of the second higher diffractive power P2.d.high to the second base refractive power P2.r to provide near or intermediate vision.

Other advantages of this configuration of IOL 210 and diffractive pattern 215 are illustrated with reference to the lower portions of FIGS. 4 and 5. In contrast to focus 120 of IOL 110, incoming rays 224 form a first focus 220 that converges or focuses to a single point or substantially a single point. The relatively sharp focus of first focus 220 is provided by configuring diffractive pattern 210 to have a negative LCA that reduces or eliminates a positive LCA of the refractive power of lens 210 and/or a positive LCA of the cornea 202 or eye 200. Again, it will be understood that illustration of first focus 220 as a point is an idealization and that in a real eye at some residual LCA or other longitudinal aberrations would typically still exist. Thus, in contrast to first IOL 110, second IOL 210 provides distant vision that has reduced or no LCA and that has improved or relatively high visual acuity and/or MTF performance.

Referring again to FIG. 4, incoming rays 224, which form second focus 222, are spread along optical axis OA2, the extent being shown by the dashed lines at the bottom of the figure. This spread may be similar to that of first focus 120 of first IOL 110. As will be seen, the spread of light in second focus 222 may result in a reduction of visual acuity or the MTF of second eye 200 for objects and light sources located at relatively near locations from eyes 100, 200. In the current embodiment, this spread of light by IOL 210 along optical axis OA2 is due to an overcorrection of the longitudinal chromatic aberration (LCA) of the refractive portion of lens 210 and/or cornea 202. In general, the spread of light along optical axis OA2 may additionally or alternatively be due to other optical effects such as spherical aberrations, astigmatism, or coma.

Referring again to FIG. 5, the collimated wavefront shown in FIG. 4 is replaced by a diverging wavefront that directs diverging rays 224 toward eye 200. Rays 224 are produced by the same source or object providing rays 124 to eye 100. In this case, second focus 222 is located at retina 204 along optical axis OA2, while first focus 220 is located posteriorly of retina 204. In contrast to focus 122 of first IOL 110, the overcorrection by diffractive pattern 215 of the negative LCA of IOL 210 and/or cornea 202 spreads the light of incoming rays 224 along optical axis OA2, at least somewhat reducing visual acuity and/or MTF performance.

By way of summary, for distant objects or light sources (FIG. 4; distant vision), IOL 210 produces a first focus 220 of eye 200 that provides a relatively sharp image that has a relatively small amount or no LCA. In this manner, second lens 210 provides distant vision that has improved visual acuity and/or MTF performance. However, for relatively close objects or light sources (FIG. 5; near or intermediate vision), IOL 210 produces a second focus 222 that is located on retina 204 and an image that is at least somewhat blurred due to relatively large LCA.

Thus, the performance of IOL 210 is advantageously configured to complement the performance of IOL 120. That is, IOL 210 produces a relatively sharp focus 220 on retina 204 of second eye 200 for collimated light or relatively distant objects or light sources. This results in distant vision for second eye 200 that has a relatively high visual acuity and/or MTF performance. This complements the performance of IOL 110, which produces a relatively blurred focus 120 on retina 104 of first eye 100 for collimated light or relatively distant objects or light sources. This results in distant vision for first eye 100 that has a visual acuity and/or MTF performance that is somewhat lower than that for second eye 200. Therefore, the combination of IOLs 110, 210 provides distant vision to a subject in which one eye has high visual acuity and/or MTF performance in one eye and somewhat lower visual acuity and/or MTF performance in the other eye.

In similar fashion, the performance of IOL 110 may be configured to complement the performance of IOL 220 for near or intermediate vision. That is, IOL 110 produces a relatively sharp focus 122 on retina 104 of first eye 100 for objects or light sources that are located relatively close to a subject. This results in near and/or intermediate vision for first eye 100 that has a relatively high visual acuity and/or MTF performance. This complements the performance of IOL 210, which produces a relatively blurred focus 222 on retina 204 of second eye 200 for objects or light sources that are located relatively close to the subject. This results in near and/or intermediate vision for second eye 200 that has a visual acuity and/or MTF performance that is somewhat lower than that for first eye 100. Therefore, the combination of IOLs 110, 210 provides near and/or intermediate vision to a subject in which one eye has high visual acuity and/or MTF performance in one eye and somewhat lower visual acuity and/or MTF performance in the other eye.

Accordingly, the combination of IOLs 110, 210 provides images having reduced or no chromatic aberrations for both distant vision (eye 200) and for near and/or intermediate vision (eye 100), along with an associated increase in optical performance for both eyes 100, 200, for example, in terms of higher visual acuity and/or MTF performance.

In general, each IOL 110, 210 may be configured with differing amount of other absolute or relative longitudinal aberrations that impact the aberrations of an incident wavefront (e.g., from the cornea of an eye) for one or more foci of each IOL. For example, the amount of a monochromatic aberration such as astigmatism or spherical aberration may be different for each IOL 110, 210. One or both IOLs 110, 210 may be configured to provide a predetermined balance between LCA and one or more monochromatic aberrations by using aspheric shapes on one or both IOLs 110, 210, as discussed above.

Exemplary structures of diffractive patterns 115, 215 for providing the above performance of the combined IOLs 110, 210 will now be discussed. Diffractive patterns 115, 215 are generally multifocal diffractive patterns producing two or more foci in the visible waveband when used in combination with refractive components of IOLs 110, 210 and/or eye 100, 200. Various methods of providing ophthalmic lenses with such diffractive patterns are known within the art including, but not limited to, U.S. Pat. Nos. 4,641,934; 4,881,804; 4,995,715; 5,144,483; 5,229,797; 7,455,404; all of which are herein incorporated by reference in their entirety.

In some embodiments, diffractive pattern 115 of first IOL 110 comprises a plurality of echelettes 108 that are configured provide a first or primary diffraction order that is a zeroth diffraction order and a second or secondary diffraction order that is a +1 diffraction order. By contrast, diffractive pattern 215 of second IOL 220 comprises a plurality of echelettes 208 that are configured provide a first diffraction order that is a +1 diffraction order and a second diffraction order that is a +2 diffraction order. In certain embodiments, the +1 diffraction orders of each diffractive pattern 115, 215 may be selected to reduce or compensate for chromatic dispersion or LCA produced by the materials and geometry of IOLs 110, 210 and/or eye (e.g., cornea). In such embodiments, the +1 diffraction orders each produce a negative LCA that is opposite in sign to a positive LCA of the refractive elements of the eye and/or IOLs 110, 210. The magnitude of the negative LCA of diffractive patterns 115, 215 may be controlled by appropriate selection of lens material and/or amount of diffractive power in the second and first diffraction orders of the diffractive patterns 115, 215, respectively (e.g., by selection of echelette spacing or area). In some embodiments, the lens material and/or amount of diffractive power of diffractive patterns 115, 215 are selected to be the same for both diffractive patterns 115, 215. Additionally, diffractive patterns 115, 215 may be selected to have the same amount of relative or absolute LCA. Alternatively, the lens material and/or amount of diffractive power of the diffractive patterns 115, 215 is different for each diffractive pattern 115, 215, for example, to provide a different amount of relative or absolute LCA for each diffractive pattern 115, 215 and/or a different amount of chromatic aberration reduction for each IOL 110, 210 and/or eye 100, 200.

When first diffractive pattern 115 has first diffraction order that is a zeroth diffraction order and second diffractive pattern 215 has first diffraction order that is a +1 diffraction order, the first diffraction order of first diffractive pattern 115 has no or zero diffractive power and therefore does not affect the positive LCA of IOL 110 or eye 100. Thus, the lower total power P1.low a total LCA that is positive. Meanwhile, the second diffraction order of second diffractive pattern 215 has diffractive power is greater than that of the first diffraction order of second diffractive pattern 215. As a result, the second diffraction order of second diffractive pattern 215 has an LCA that is even more negative than the negative LCA of the first diffraction order. Thus, the negative LCA of the second diffraction order for IOL 210 may either further reduce the positive LCA of IOL 210 and/or eye 200, if the negative LCA of the first diffraction order is relatively low.

Alternatively, the negative LCA of the second diffraction order for IOL 210 may be configured to overcompensate the positive LCA of IOL 210 and/or eye 200. In some embodiments, the diffractive pattern 215 is configured so that the first diffraction order slightly under compensates for the positive LCA of IOL 210 and/or eye 200, while the second diffraction order slightly overcompensates for the positive LCA of IOL 210 and/or eye 200. The amount of overcompensation may be equal, or about equal, to the amount of under compensation. Alternatively, the amount of overcompensation and the amount of under compensation may be different, for example, the amount of over compensation of one IOL and/or eye differing less than 10 percent, less than 20 percent, or less than 50 percent from the amount of under compensation of the other IOL and/or eye.

In some embodiments, first diffractive pattern 115 has first diffraction order that is a +1 diffraction order and a second diffraction order that is a +2 diffraction order, while second diffractive pattern 215 has first diffraction order that is a +2 diffraction order and a second diffraction order that is a +3 diffraction order. In some embodiments, at least one of diffractive patterns 115, 215 may be a monofocal diffractive pattern, be configured as a high MOD diffractive pattern, comprise echelettes having varying step sizes, or have other diffractive configurations known in the art.

While formation of diffractive patterns 115, 215 may be provided by forming echelettes onto a surface of IOLs 110, 210, other methods of realization are anticipated. For example, either or both diffractive patterns 115, 215 may be formed of a material having a refractive index and/or optical density that changing with radial distance from the lens optical axis. Such patterns may be produced holographically and/or by techniques such a UV curing a lens material in a manner that varies the exposure of UV with radius.

The amount of LCA of each IOL 110, 210, or each diffraction order or focus 120, 122, 220, 222, may be selected to provide a predetermined balance of image quality between the different eyes 100, 200 and the different foci or images produced in each eye 100, 200. For example, one or both IOLs 110, 210 may be achromatic for one of the foci thereof, or may provide an achromatic system that includes eye 100, 200 when IOL 110, 210 is disposed within eye 100, 200.

In some embodiments, at least one of the IOLs 110, 210 has a negative LCA for one of its foci that changes a positive of the combination of the IOL and the eye or cornea. For example, at least one of IOLs 10, 210 may have a predetermined LCA that is greater than a positive LCA of the cornea, whereby the positive LCA of a cornea or eye is at least partially reduced. The amount of correction or change provided by each IOL 110, 210 may be the same or about the same. Alternatively, the correction or change may be different for each IOL 100, 200 so that a desired balance between the foci 120, 122, 220, 222 may be achieved. For example, first IOL 110 may have a LCA that reduces and under corrects for a positive LCA the cornea, while second IOL 210 has a LCA that overcorrects for a positive LCA of eye 200. In other embodiments, the higher diffraction order of first diffractive pattern 115 may have a LCA that reduces a LCA of first lens shape 112 only and/or the lower diffraction order of second diffractive pattern 215 may have a LCA that reduces a LCA of second lens shape 212 only.

IOLs 110, 210 may be configured so that the absolute or relative LCA is the same, or about the same, for the first diffraction order of IOL 210 (corresponding to P2.low) and the second diffraction order of IOL 110 (corresponding to P1.high). Additionally or alternatively, IOLs 110, 210 may be configured so that focuses 120 and 222 have the same amount, or about the same amount, of absolute or relative LCA. For example, absolute or relative LCA may be within 5%, 10%, 20%, 50% of one another between the two IOLs 110, 210, or between the two eyes 100, 200 when IOLs 110, 210 are implanted.

In other embodiments, IOLs 110, 210 have different amounts of absolute or relative LCA. For example, IOL 110 may be configured so that P1.high and/or focus 122 have an absolute or relative LCA that is zero, or about zero (e.g., a relative LCA that is less than 5%, less than 2%, or less than 1%). By contrast, IOL 210 may be configured in such embodiments so that P2.low and P2.high, and/or focus 220 and focus 222, both have some LCA. For example, both P2.low and P2.high, and/or focus 220 and focus 222, may have the same amount, or about the same amount (e.g., within 5%, 10%, 20%, 50%), of absolute or relative LCA. Such a balance of LCA for the two foci of IOL 210 may allow both to have some LCA, but less than if one of the focuses were configured to minimize LCA.

IOLs 110, 210 may be configured as custom lenses for the eyes of a particular subject. Alternatively, the design of IOLs 110, 210, sets of such lens pairs, may be based on one or more eye models that take into account physical and optical characteristics for a given population, for example, as disclosed in U.S. Pat. Nos. 6,609,793 or 7,377,640, which are herein incorporated by reference in their entirety. For example, a model cornea may be based on the Navarro eye model, as disclosed in "Accommodation-dependent model of the human eye with aspherics", J. Opt. Soc. Am. A, Vol. 2, No. 8, pp. 1273-1281, which is herein incorporated in its entirety. In some embodiments, the cornea may be characterized by Equations (1) above, where the pupil has a 5 millimeter diameter, the model cornea has a radius of curvature of 7.553 millimeters and a conic constant of −0.1034, and the eye has a refractive index 1.3375, as disclosed in U.S. Pat. No. 6,609,793.

In certain embodiments, a mathematical representation of one or both IOLs 110, 210 is included in or added to an eye model, a LCA of the model eye associated with first higher diffractive power P1.d.high is approximately zero, while a LCA of the model eye associated with first higher diffractive power P1.d.high is positive. In one embodiment, the model eye includes a model cornea having a 6 millimeter diameter and an anterior surface shape characterized by a conoid of rotation with a radius of 7.575 millimeters and a conic constant of −0.14135. The model lens 110, 210 has an anterior surface apex located 3.6 millimeters in a posterior direction from an apex of the model cornea. The model eye has an image plane located 26.42 millimeters in a posterior direction from the anterior surface apex and a refractive index of 1.3375 and a refractive index of 1.0 for the media anterior to model cornea.

In certain embodiments, the difference between the first and second diffraction orders of one or both IOLs 110, 210 represents an add power for each IOL or eye. The add power may be at least 1 Diopter or 2 Diopters (e.g., to provide intermediate vision) or at least 3 Diopters or 4 Diopters (e.g., to provide near vision). The add power may be the same for both IOLs 110, 210. Alternatively, the add power of IOL 110 may be different than the add power for IOL 210, for example, differing by at least 0.5 Diopters, at least 1 Diopter, or at least 2 Diopters.

Diffractive patterns 115, 215 of IOLs 110, 210 may be configured so that the two diffraction orders of each IOL is the same or about the same (e.g., within 2% or 5%). Alternatively, one or both IOLs 110, 210 may have a different split between the two diffraction orders, for example, a 30%:70% split between the two diffraction orders of the IOL. For example, IOL 110 and/or IOL 210 may be configured so that more energy is in the focus or diffraction order that has the lower LCA (e.g., focus 122 and focus 220 in the embodiment illustrated in FIGS. 4 and 5). The diffraction efficiencies of the two diffraction orders of IOLs 110, 210 may be the same for both IOLs. Alternatively, IOL 210 may have a different efficiency split between its two diffraction orders than the split for the IOL 110. The various diffraction efficiencies discussed in this paragraph may be for a broadband or white light source. Alternatively, the diffraction efficiencies may be for a more narrow frequency bandwidth (e.g., for green light) or at a single wavelength (e.g., at 550 nanometers).

IOLs 110, 210 may be manufactured using molding and/or machining techniques known in the art. IOLs 110, 210 may generally be constructed of any of the various types of material known in the art. For example, IOLs 110, 210 may be a foldable lens made of at least one of the materials commonly used for resiliently deformable or foldable optics, such as silicone polymeric materials, acrylic polymeric materials, hydrogel-forming polymeric materials (e.g., polyhydroxyethylmethacrylate, polyphosphazenes, polyurethanes, and mixtures thereof), or the like. Other advanced formulations of silicone, acrylic, or mixtures thereof are also anticipated. The lens material may be selected to have a relatively high refractive index, and thus provide a relatively thin optic, for example, having a center thickness in the range of about 150 microns to about 1000 microns, depending on the material and the optical power of the lens. At least portions of IOLs 110, 210, for example one or more haptics or fixation members thereof, may be constructed of a more rigid material including such polymeric materials as polypropylene, polymethylmethacrylate PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. In some embodiments, the optic and haptic portions of IOLs 110, 210 are each integrally formed of a single common material.

Once IOLs 110, 210 are manufactured, they are preferably packaged in a sterile environment. IOLs 110, 210 may be custom fabricated for a particular subject upon receipt of an order from a hospital, clinic, doctor's office, or other facility or individual. Upon receipt of an order, IOLs 110, 210 are fabricated and shipped the manufacturer either separately or as a pair. In some embodiments, one or more backup lenses may also be shipped. In some embodiments, IOLs 110, 210 are produced in a variety of optical powers for storage under appropriate conditions. In addition, lenses having different values of other parameters may be manufactured and store. For example, lenses having different amounts of cylinder power, spherical aberration, LCA, and/or the like may be manufactured. One or both IOLs 110, 210 may be selected from a catalog or listing of stock lenses that cover standard spherical powers, cylinder powers, add powers, shape factors, monochromatic aberrations (e.g., spherical aberration), amounts of LCA, and/or the like.

IOLs 110, 210 may be configured by a manufacturer, supplier, or distributor in the form of a kit or set of IOLs that may be ordered and/or shipped together for use in the two eyes of a subject. The lenses may packaged, stored, and/or shipped together in separate compartments of a single container for shipment. Alternatively, IOLs 110, 210 are ordered as a set and shipped separately and/or at different times appropriate for scheduled surgery dates for each eye 100, 200. For example, a practitioner may order and/or receive one of the IOLs 110, 210 for implantation in one of the eyes of a subject, then later order and/or receive the other IOLs 210, 110 for implantation in the other eye of the subject. Alternatively, the two IOLs are specified and/or ordered at the same time, but shipped and delivered separately as needed for implantation into each eye of the subject.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of providing a system of ophthalmic lenses, comprising:
    providing a first lens for a first eye of a subject, the first lens comprising a first lens shape having a first base refractive power and a first multifocal diffractive pattern imposed on the first lens shape, the first lens including a first lower optical power and a first higher optical power that is greater than the first lower optical power, the first lower optical power being equal to a sum of the first base refractive power and a first lower diffractive power of a first lower diffraction order of the first diffractive pattern, the first higher optical power being equal to a sum of the first base refractive power and a first higher diffractive power of a first higher diffraction order of the first diffractive pattern; and
    providing a second lens for a second eye of the subject, the second lens comprising a second lens shape having a second base refractive power and a second multifocal diffractive pattern imposed on the second lens shape, the second lens including a second lower optical power and a second higher optical power that is greater than the second lower optical power, the second lower optical power being equal to a sum of the second base refractive power and a second lower diffractive power of a second lower diffraction order of the second diffractive pattern, the second higher optical power being equal to a sum of the second base refractive power and a second higher diffractive power of a second higher diffraction order of the second diffractive pattern;
    wherein the first higher optical power has a negative longitudinal chromatic aberration (LCA) and the second lower optical power has a negative LCA; and wherein the first lens has a LCA that, for light passing through a first cornea of the first eye, reduces and under corrects for a positive LCA of the first cornea when the first lens is placed in or on the first eye, and the second lens has a LCA that, for light passing through a second cornea of the second eye, overcorrects for a positive LCA of the second cornea when the second lens is placed in or on the second eye; wherein the overcorrection and the under correction have a difference of less than 20 percent.

2. The method of claim 1, further comprising packaging the first lens and the second lens into a kit and delivering the kit to a supplier of ophthalmic lenses or to a facility that uses the lenses to provide corrected vision to a subject.

3. The method of claim 1, further comprising packaging the first lens and the second lens into a kit and delivering the kit to a supplier of ophthalmic lenses or to a facility that implants the lenses into a first eye and second eye, respectively, of a subject.

4. The method of claim 1, further comprising delivering one of the first lens and the second lens to a facility for delivery onto or into a first eye of a subject, subsequently delivering the other of the first lens and the second lens to the facility for delivery onto or into a second eye of a subject.

5. A method of correcting an optical system, comprising:
    specifying a first lens for a first eye of a subject, the first lens comprising a first lens shape having a first base refractive power and a first multifocal diffractive pattern imposed on the first lens shape, the first lens including a first lower optical power and a first higher optical power that is greater than the first lower optical power, the first lower optical power being equal to a sum of the first base refractive power and a first lower diffractive power of a first lower diffraction order of the first diffractive pattern, the first higher optical power being equal to a sum of the first base refractive power and a first higher diffractive power of a first higher diffraction order of the first diffractive pattern; and
    specifying a second lens for a second eye of the subject, the second lens comprising a second lens shape having a second base refractive power and a second multifocal diffractive pattern imposed on the second lens shape, the second lens including a second lower optical power and a second higher optical power that is greater than the second lower optical power, the second lower optical power being equal to a sum of the second base refractive power and a second lower diffractive power of a second lower diffraction order of the second diffractive pattern, the second higher optical power being equal to a sum of the second base refractive power and a second higher diffractive power of a second higher diffraction order of the second diffractive pattern, the first higher optical power has a negative longitudinal chromatic aberration (LCA) and the second lower optical power has a negative LCA, wherein the first lens has a LCA that, for light passing through a first cornea of the first eye, reduces and under corrects for a positive LCA of the first cornea when the first lens is placed in or on the first eye, and the second lens has a LCA that, for light passing through a second cornea of the second eye, overcorrects for a positive LCA of the second cornea when the second lens is placed in or on the second eye; wherein the overcorrection and the under correction have a difference of less than 20 percent.

* * * * *